(12) United States Patent
Jones

(10) Patent No.: US 7,419,698 B2
(45) Date of Patent: Sep. 2, 2008

(54) PRECURSORS FOR CHEMICAL VAPOR DEPOSITION

(75) Inventor: Anthony Copeland Jones, Eccleston Park (GB)

(73) Assignee: Sigma-Aldrich Co., St. Louis, MO (US)

( * ) Notice: Subject to any disclaimer, the term of this patent is extended or adjusted under 35 U.S.C. 154(b) by 259 days.

(21) Appl. No.: 10/493,667

(22) PCT Filed: Oct. 25, 2002

(86) PCT No.: PCT/GB02/04822

§ 371 (c)(1),
(2), (4) Date: Aug. 31, 2004

(87) PCT Pub. No.: WO03/035926

PCT Pub. Date: May 1, 2003

(65) Prior Publication Data

US 2005/0008781 A1    Jan. 13, 2005

(30) Foreign Application Priority Data

Oct. 26, 2001    (GB) .................. 0125724.5
Dec. 4, 2001    (GB) .................. 0129080.8

(51) Int. Cl.
*C23C 16/00*    (2006.01)

(52) U.S. Cl. .............. 427/248.1; 427/255.36; 556/51

(58) Field of Classification Search ............ 556/51; 427/248.1, 255.36; *C23C 16/00*
See application file for complete search history.

(56) References Cited

U.S. PATENT DOCUMENTS

| | | | | |
|---|---|---|---|---|
| 4,758,682 A * | 7/1988 | Collins et al. | ............... | 556/137 |
| 5,344,948 A * | 9/1994 | Verkade | ............... | 556/51 |
| 5,395,954 A * | 3/1995 | Soria et al. | ............... | 556/10 |
| 5,464,656 A * | 11/1995 | Verkade | ............... | 427/248.1 |
| 5,508,458 A * | 4/1996 | Zhao | ............... | 556/45 |
| 5,527,752 A * | 6/1996 | Reichle et al. | ............... | 502/117 |
| 5,698,022 A * | 12/1997 | Glassman et al. | ............... | 106/287.18 |
| 5,814,574 A * | 9/1998 | McNally | ............... | 502/103 |
| 5,830,530 A * | 11/1998 | Jones | ............... | 427/248.1 |
| 5,863,836 A * | 1/1999 | Jones | ............... | 438/681 |
| 5,886,203 A * | 3/1999 | Jones et al. | ............... | 556/96 |
| 5,900,498 A * | 5/1999 | Winter et al. | ............... | 556/51 |
| 5,908,947 A * | 6/1999 | Vaartstra | ............... | 556/42 |
| 5,980,978 A * | 11/1999 | Jones et al. | ............... | 438/46 |
| 6,159,855 A * | 12/2000 | Vaartstra | ............... | 438/681 |
| 6,248,928 B1 * | 6/2001 | Jones | ............... | 568/318 |
| 6,277,436 B1 * | 8/2001 | Stauf et al. | ............... | 427/126.3 |
| 6,280,518 B1 * | 8/2001 | Itsuki et al. | ............... | 106/287.19 |
| 6,313,035 B1 * | 11/2001 | Sandhu et al. | ............... | 438/681 |
| 6,376,691 B1 * | 4/2002 | Celinska et al. | ............... | 556/28 |
| 6,383,669 B1 * | 5/2002 | Leedham et al. | ............... | 428/702 |
| 6,485,784 B1 * | 11/2002 | Leedham et al. | ............... | 427/255.31 |
| 6,552,209 B1 * | 4/2003 | Lei et al. | ............... | 556/42 |
| 6,623,656 B2 * | 9/2003 | Baum et al. | ............... | 252/62.9 PZ |
| 6,627,765 B2 * | 9/2003 | Giolando | ............... | 556/90 |
| 6,689,427 B2 * | 2/2004 | Min et al. | ............... | 427/592 |
| 6,946,395 B2 * | 9/2005 | Marsh | ............... | 438/686 |

FOREIGN PATENT DOCUMENTS

| | | |
|---|---|---|
| EP | 614867 | 9/1994 |
| JP | 2001-181288 A | 7/2001 |
| JP | 2002069641 | 3/2002 |

OTHER PUBLICATIONS

Chemical Abstracts, vol. 80, No. 53, Jun. 10, 1974, Columbus, OH, US; abstract No. 132732, Bharara, P.C. et al. "Reactions of titanium alkoxides with (methylamino) alchohols". XP002236947, abstract & Zeitschrift Fuer Anorganische Und Allgemeine Chemie (1974), 403(3), 337-346, 1974.

* cited by examiner

*Primary Examiner*—Bret Chen
(74) *Attorney, Agent, or Firm*—Harness, Dickey, & Pierce PLC; J. Timothy Keane

(57) ABSTRACT

Ti, Zr Hf and La precursors for use in MOCVD techniques have a ligand of the general formula $OCR^1(R^2)CH_2X$, wherein $R^1$ is H or an alkyl group, $R^2$ is an optionally substituted alkyl group and X is selected from OR and $NR_2$, wherein R is an alkyl group or a substituted alkyl group.

19 Claims, 3 Drawing Sheets

PRECURSORS FOR CHEMICAL VAPOR DEPOSITION

This application is the U.S. National Phase of PCT/GB02/04822 filed 24 Oct. 2002, which claims priority to Great Britain Patent Application Ser. No. GB 0125724.5, filed 26 Oct. 2001 and Great Britain Patent Application Ser. No. GB 0129080.8, filed 4 Dec. 2001.

This invention concerns precursors for chemical vapour deposition. This invention is particularly, but not exclusively concerned with precursors for the growth of zirconium oxide ($ZrO_2$), hafnium oxide ($HfO_2$), zirconium oxide/silicon oxide (ZSO) and hafnium oxide/silicon oxide (HSO) by chemical vapour deposition.

Thin films of $ZrO_2$ and $HfO_2$ and the related silicates ZSO and HSO have important technological applications. In particular, they have high permittivities and are relatively stable in contact with silicon, making them the prime candidates to replace $SiO_2$ as gate dielectric layers in next-generation MOSFET devices in integrated Si circuits. Metalorganic chemical vapour deposition (MOCVD) is an attractive technique for the deposition of these materials, offering the potential for large area growth, good composition control and film uniformity, and excellent conformal step coverage at device dimensions less than 2 μm, which is particularly important in microelectronics applications.

An essential requirement for a successful MOCVD process is the availability of precursors with the appropriate physical properties for vapour phase transport and a suitable reactivity for deposition. There must be an adequate temperature window between evaporation and decomposition, and for most electronics applications oxide deposition is restricted to temperatures in the region of 500° C., to prevent degradation of the underlying silicon circuitry and metal interconnects.

There are a number of problems associated with existing Zr and Hf CVD precursors. For instance, the halides $ZrCl_4$ and $HfCl_4$ are low volatility solids which need substrate temperatures of 800° C. and above for oxide deposition. Metal β-diketonates, such as [$Zr(thd)_4$] (thd=2,2,6,6-tetramethylheptane-3,5-dionate) also require high substrate temperatures (>600° C.) for oxide growth. These are incompatible with the requirements of the electronics industry. Metal alkoxides are more attractive CVD precursors as they allow lower deposition temperatures. However, the majority of [$Zr(OR)_4$] and [$Hf(OR)_4$] complexes are dimeric or polymeric with limited volatility, due to the pronounced tendency of the Zr(IV) and Hf(IV) to expand their coordination sphere to six, seven or eight. In order to inhibit oligomerisation, sterically demanding ligands such as tert-butoxide have been employed, and [$Zr(OBu^t)_4$] (D. C. Bradley, Chem. Rev. 1989, 89, 1317) and [$Hf(OBu^t)_4$] (S. Pakswer & P Skoug, in "Thin dielectric oxide films made by oxygen assisted pyrolysis of alkoxides", The Electrochem. Soc., Los Angeles, Calif., USA, 1970, 619-636) have been successfully used for the CVD of $ZrO_2$ and $HfO_2$. However, these mononuclear precursors contain unsaturated four-coordinate metal centres and the tert-butoxide ligand undergoes a catalytic decomposition reaction in the presence of trace water. This makes them highly air and moisture sensitive and susceptible to pre-reaction in the CVD reactor. Their reactivity also leads to a greatly reduced shelf life, especially in solution-based liquid injection CVD applications.

An object of this invention is to provide stable and volatile Ti, Zr and Hf precursors suitable for use in chemical vapour deposition techniques.

It has been surprisingly found that the donor functionalised alkoxy ligand 1-methoxy-2-methyl-2-propanolate [$OCMe_2CH_2OMe$, mmp] is effective in inhibiting oligomerisation in Zr and Hf alkoxide complexes, as well as increasing the ambient stability of the complexes.

Accordingly the present invention provides Ti, Zr, Hf and La precursors for use in MOCVD techniques having a ligand of the general formula $OCR^1(R^2)CH_2X$, wherein $R^1$ is H or an alkyl group, $R^2$ is an optionally substituted alkyl group and X is selected from OR and $NR_2$, wherein R is an alkyl group or a substituted alkyl group.

Precursors according to a first preferred embodiment of the invention have the following general formula:

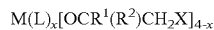

$$M(L)_x[OCR^1(R^2)CH_2X]_{4-x}$$

wherein M is a metal selected from Ti, Zr and Hf, L is a ligand, x is a number from 0 to 3 and $R^1$, $R^2$ and X are as defined above.

The preferred ligand L is an alkoxy group having from 1 to 4 carbon atoms, of which tertiary-butoxide ($OBu^t$) group is most preferred, although other groups such as iso-propoxide ($OPr^i$) can be employed.

The preferred ligand of the formula $OCR^1(R^2)CH_2X$ is 1-methoxy-2-methyl-2-propanolate (mmp) but other donor functionalised alkoxide ligands may also carry out the desirable function of inhibiting oligomerisation in Zr, Hf and Ti alkoxides for use in the invention. These include but are not limited to $OCH(Me)CH_2OMe$, $OCEt_2CH_2OMe$, $OCH(Bu^t)CH_2OEt$, $OC(Bu^t)_2CH_2OEt$, $OC(Pr^i)_2CH_2OEt$, $OCH(Bu^t)CH_2NEt_2$, $OC(Pr^i)_2CH_2OC_2H_4OMe$ and $OC(Bu^t)(CH_2OPr^i)_2$.

The invention further provides a method of making Ti, Zr and Hf precursors for use in MOCVD techniques comprising reacting mmpH with the corresponding metal alkoxide or metal alkylamide in appropriate molar proportions.

The new alkoxide complexes $Zr(OBu^t)_2(mmp)_2$, $Zr(mmp)_4$, $Hf(OBu^t)_2(mmp)_2$, and $Hf(mmp)_4$ have been synthesised by the addition of mmpH to $Zr(OBu^t)_4$ and $Hf(OBu^t)_4$ in appropriate molar proportions. The complexes have high vapour pressures suitable for MOCVD, and are also much less reactive to air and moisture than $Zr(OR)_4$ compounds, wherein R is an alkyl group, making them easier to handle and use in MOCVD. The reduced air-sensitivity of these new Zr and Hf complexes arises from the replacement of the highly moisture sensitive tert-butoxide groups in [$Zr(OBu^t)_4$] and [$Hf(OBu^t)_4$] with the mmp ligand, which is much less susceptible to hydrolysis. The complexes are further stabilised to hydrolysis by an increase in the coordination number of the central Zr or Hf atom.

According to a second preferred embodiment the invention can be extended to other metals, which have large atomic radii and are highly positively charged, such as lanthanum, in which case preferred precursors have the following general formula

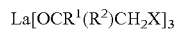

$$La[OCR^1(R^2)CH_2X]_3$$

wherein $R^1$ is H or an alkyl group, $R^2$ is an optionally substituted alkyl group and X is selected from OR and $NR_2$, wherein R is an alkyl group or a substituted alkyl group.

The preferred ligand for this preferred embodiment of the invention is 1-methoxy-2-methyl-2-propanolate [$OCMe_2CH_2OMe$], although other donor functionalised alkoxide ligands may be used. These may include but are not limited to $OCH(Me)CH_2OMe$, $OCEt_2CH_2OMe$, $OCH(Bu^t)CH_2OEt$, $OC(Bu^t)_2CH_2OEt$, $OC(Pr^i)_2CH_2OEt$, $OCH(Bu^t)CH_2NEt_2$, $OC(Pr^i)_2CH_2OC_2H_4OMe$ and $OC(Bu^t)(CH_2OPr^i)_2$.

The invention also provides a preferred method of making precursors according to the second preferred embodiment comprising reacting mmpH with La{N(SiMe$_3$)$_2$}$_3$ in appropriate molar proportions.

Precursors according to the invention may be used in depositing single or mixed oxide layers or films by conventional MOCVD, in which the precursor is contained in a metalorganic bubbler, or by liquid injection MOCVD, in which the precursor is dissolved in an appropriate inert organic solvent and then evaporated into the vapour phase using a heated evaporator. The precursors may also be suitable for use in the deposition of zirconium oxide, hafnium oxide and titanium oxide films by other chemical vapour deposition techniques, such as atomic layer deposition (ALD).

The precursors can be used for the MOCVD of ZrO$_2$, HfO$_2$, and TiO$_2$, La$_2$O$_3$, and in combination with other precursors for the MOCVD of complex oxides containing zirconium oxide, hafnium oxide, and lanthanum oxide such as ZSO and HSO and La-silicate.

The precursors can also be used in combination for the MOCVD of complex oxides. Examples include the MOCVD of bismuth-titanate from the combinations Bi(mmp)$_3$/Ti(OPr$^i$)$_2$(mmp)$_2$ or Bi(mmp)$_3$/Ti(mmp)$_4$.

The invention will now be further described with reference to the accompanying drawings, in which.

The invention will now be further described by means of the following Examples.

EXAMPLE 1

Preparation of Zr(OBu$^t$)$_2$(mmp)$_2$ 2.8 ml (2.69 g, 7.0 mmol) Zr(OBu$^t$)$_4$ was dissolved in hexane (ca. 40 ml). mmph (1.6 ml, 1.44 g, 13.9 mmol) was added dropwise, the mixture was heated to reflux and stirring continued for a further 2 hours. The solution was cooled to room temperature and the volatiles removed by evaporation under reduced pressure. The product was recrystallised from hexane to give a white crystalline solid.

M.pt.: 96-101° C. (uncorrected) Microanalysis: Calc. C: 48.71; H: 9.10. Found: C: 46.32; H, 8.77%

$^1$H NMR: (400 MHz, d$_8$-tol) 1.19 (s, 12H, OC(CH$_3$)$_2$CH$_2$OCH$_3$), 1.37 (s, 18H, OC(CH$_3$)$_3$), 3.23 (s, 4H, OC(CH$_3$)$_2$CH$_2$OCH$_3$), 3.40 (s, 6H, OC(CH$_3$)$_2$CH$_2$OCH$_3$).

$^{13}$C NMR: 34.1 (OC(CH$_3$)$_2$CH$_2$OCH$_3$), 38.5 (OC(CH$_3$)$_3$), 65.4 (OC(CH$_3$)$_2$CH$_2$OCH$_3$), 78.6 (OC(CH$_3$)$_2$CH$_2$OCH$_3$ and OC(CH$_3$)$_3$), 90.5 (OC(CH$_3$)$_2$CH$_2$OCH$_3$).

IR: (ν cm$^{-1}$, Nujol, NaCl) 3588(w), 3442(w), 2725(m), 2360(w), 1356(s), 1277(m), 1227(m), 1206(s), 1177(s), 1115(s), 1080(s), 1012(s), 974(s), 936(s), 801(s), 782(s), 595(s).

Figure 1:
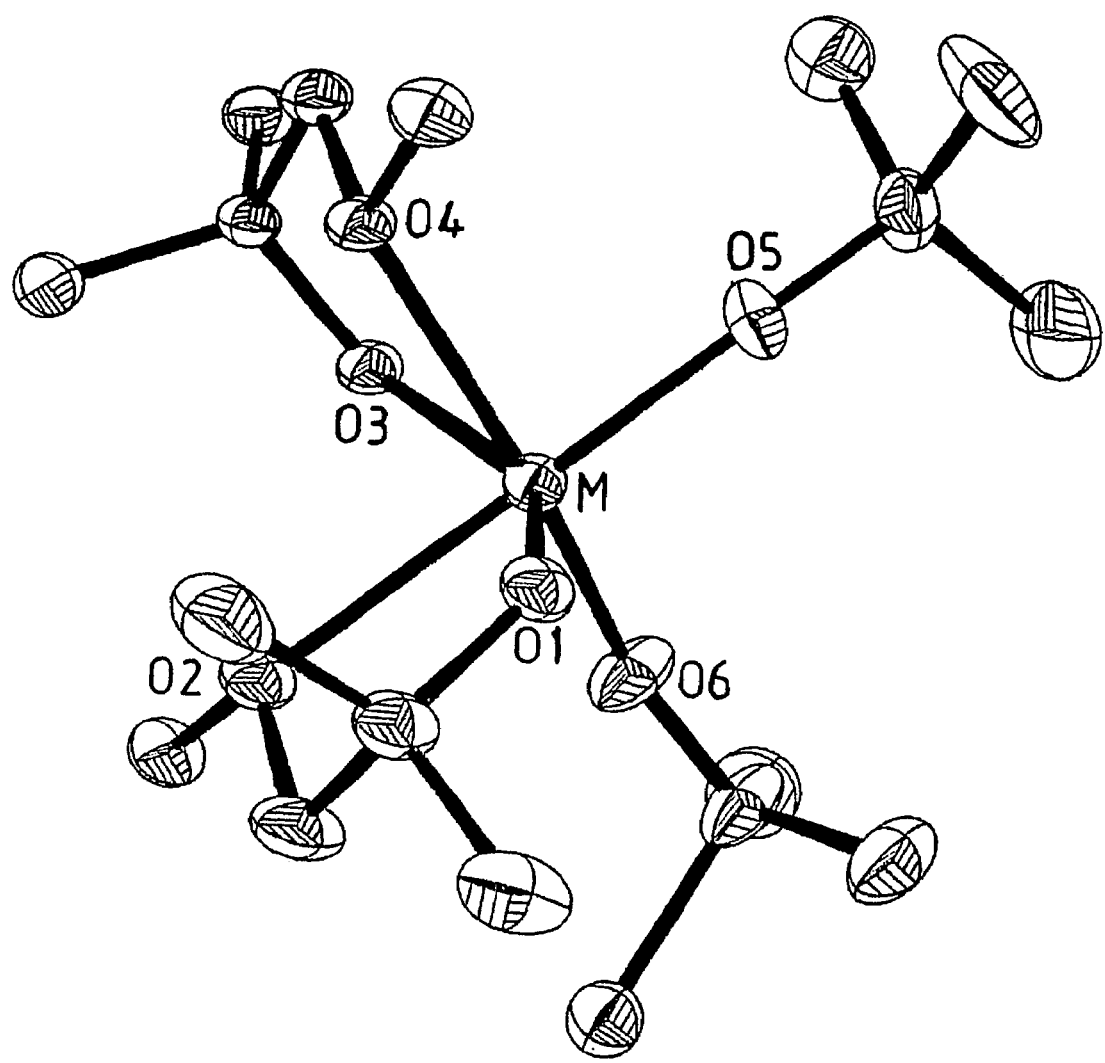
FIG. 1 shows an envisaged structure for M(OBu$^t$)$_2$(mmp)$_2$ (M=Zr or Hf)

An envisaged structure for Zr(OBu$^t$)$_2$(mmp)$_2$ is shown in FIG. 1 of the drawings.

EXAMPLE 2

Preparation of Zr(mmp)$_4$ 2.0 g (5.2 mmol) Zr(OPr$^i$)$_4$·Pr$^i$OH was dissolved in hexane (ca. 40 ml). mmpH (2.6 ml, 2.35 g, 22.5 mmol) was added dropwise, the mixture heated to reflux and stirring was continued for 2 hours. The mixture cooled to room temperature and the volatiles was removed by evaporation under reduced pressure to give the product as a white viscous oil. (Yield: 2.4 g, 94%).

Zr(mmp)$_4$ can also be synthesised from the corresponding zirconium alkylamide complexes, Zr(NR$_2$)$_4$. For instance, by the dropwise addition of mmpH (6.9 g, 65.8 mmol) to a stirred solution of [Zr(NEt$_2$)$_4$] (5.0 g, 13.2 mmol) in hexane (50 cm$^3$). The mixture was boiled under reflux for 2 hr. and then allowed to cool to room temperature. Volatiles were removed in vacuo to give the product (yield 6.25 g, 94%).

Microanalysis: Calc. C: 47.67; H: 8.82 Found: C:47.80; H: 8.79%.

$^1$H NMR: (400 MHz, d$_8$-tol): 1.21 (s, OC(CH$_3$)$_2$CH$_2$OCH$_3$), 3.16 (s, OC(CH$_3$)$_2$CH$_2$OCH$_3$), 3.27 (s, OC(CH$_3$)$_2$CH$_2$OCH$_3$)

$^{13}$C NMR: (100 MHz, d$_8$-tol): 32.1 (OC(CH$_3$)$_2$CH$_2$OCH$_3$), 64.8 (OC(CH$_3$)$_2$CH$_2$OCH$_3$), 76.0 (OC(CH$_3$)$_2$CH$_2$OCH$_3$), 88.5 (OC(CH$_3$)$_2$CH$_2$OCH$_3$).

IR: (ν cm$^{-1}$, Nujol, NaCl) 3589(w), 3448(w,br), 2724(m), 2346(w), 1377(s), 1322(m), 1279(m), 1239(m), 1176(s), 1134(m), 1114(s), 1081(m), 1018(s), 996(m), 982(s), 958(m), 937(m), 917(m), 845(m), 804(m), 784(m), 594(s).

EXAMPLE 3

Preparation of Hf(OBu$^t$)$_2$(mmp)$_2$ 3.5 ml (4.0 g, 8.5 mmol) Hf(OBu$^t$)$_4$ was dissolved in hexane (ca. 40 ml) to give a yellow solution. MmpH (2.0 ml, 1.79 g, 19.0 mmol) was added dropwise, the mixture heated to reflux and stirring continued for 2 hours. The solution was allowed to cool and the volatiles removed by boiling under reduced pressure. The crude product was recrystallised from hexane to give a white crystalline solid.

(Yield: 4.4 g, 97%).

M. Pt: 100-104° C. (uncorrected)

Microanalysis: Calc. C: 40.71; H: 7.61. Found. C: 38.93; H: 7.30%

$^1$H NMR: (400 MHz, d$_8$-tol): δ=1.18 (s, 12H, OC(CH$_3$)$_2$CH$_2$OCH$_3$), 1.38 (s, 18H, OC(CH$_3$)$_3$), 3.21 (s, 12H, OC(CH$_3$)$_2$CH$_2$OCH$_3$), 3.42 (s, 12H, OC(CH$_3$)$_2$CH$_2$OCH$_3$)

$^{13}$C NMR: (100 MHz d$_8$-tol): δ=34.4 (OC(CH$_3$)$_2$CH$_2$OCH$_3$), 38.6 (OC(CH$_3$)$_3$), 65.7, (OC(CH$_3$)$_2$CH$_2$OCH$_3$), 78.0, 79.1 (OC(CH$_3$)$_2$CH$_2$OCH$_3$ and OC(CH$_3$)$_3$), 90.9 (OC(CH$_3$)$_2$CH$_2$OCH$_3$), IR: (ν cm$^{-1}$, Nujol, NaCl): 3441 (w), 2726(m), 2256(w), 1272(s), 1177(s), 1074(s), 1016(s), 976(s), 802(s), 782(s), 593(s).

An envisaged structure for Hf(OBu$^t$)$_2$(mmp)$_2$ is shown in FIG. 1 of the drawings.

EXAMPLE 4

Preparation of Hf(mmp)$_4$ 4.0 ml (5.56 g, 11.9 mmol) [Hf(NEt$_2$)$_4$] was dissolved in hexane (60 ml). Hmmp (7.0 ml, 6.3 g, 60 mmol) was added dropwise and the mixture refluxed for 90 mins. Volatiles were removed in vacuo to give the product as a yellow viscous oil.

(Yield: 6.88 g, 97.5%).

Microanalysis: Calc. C: 40.63; H: 7.52. Found. C39.85; H 7.32%

$^1$H NMR: 1.30 (s, 24H, OC(CH$_3$)$_2$CH$_2$OCH$_3$), 3.28 (s, 8H, OC(CH$_3$)$_2$CH$_2$OCH—$_3$), 3.36 (s, 12H, OC(CH$_3$)$_2$CH$_2$OCH$_3$)

$^{13}$C NMR: 34.74 (OC(CH$_3$)$_2$CH$_2$OCH$_3$), 65.16 (OC(CH$_3$)$_2$CH$_2$OCH$_3$), 79.83 (OC(CH$_3$)$_2$CH$_2$OCH$_3$), 90.25 (OC(CH$_3$)$_2$CH$_2$OCH$_3$)

IR: (Nujol/NaCl): 3585(w), 3450(w,br), 2722(m), 1366(s), 1356(vs), 1268(s), 1242(s), 1214(vs), 1177(vs), 1115(vs), 1079(vs), 1045(vs), 1026(vs), 996(vs), 975(vs), 936(vs), 912(m), 802(s), 779(s), 594(vs).

Figure 2:
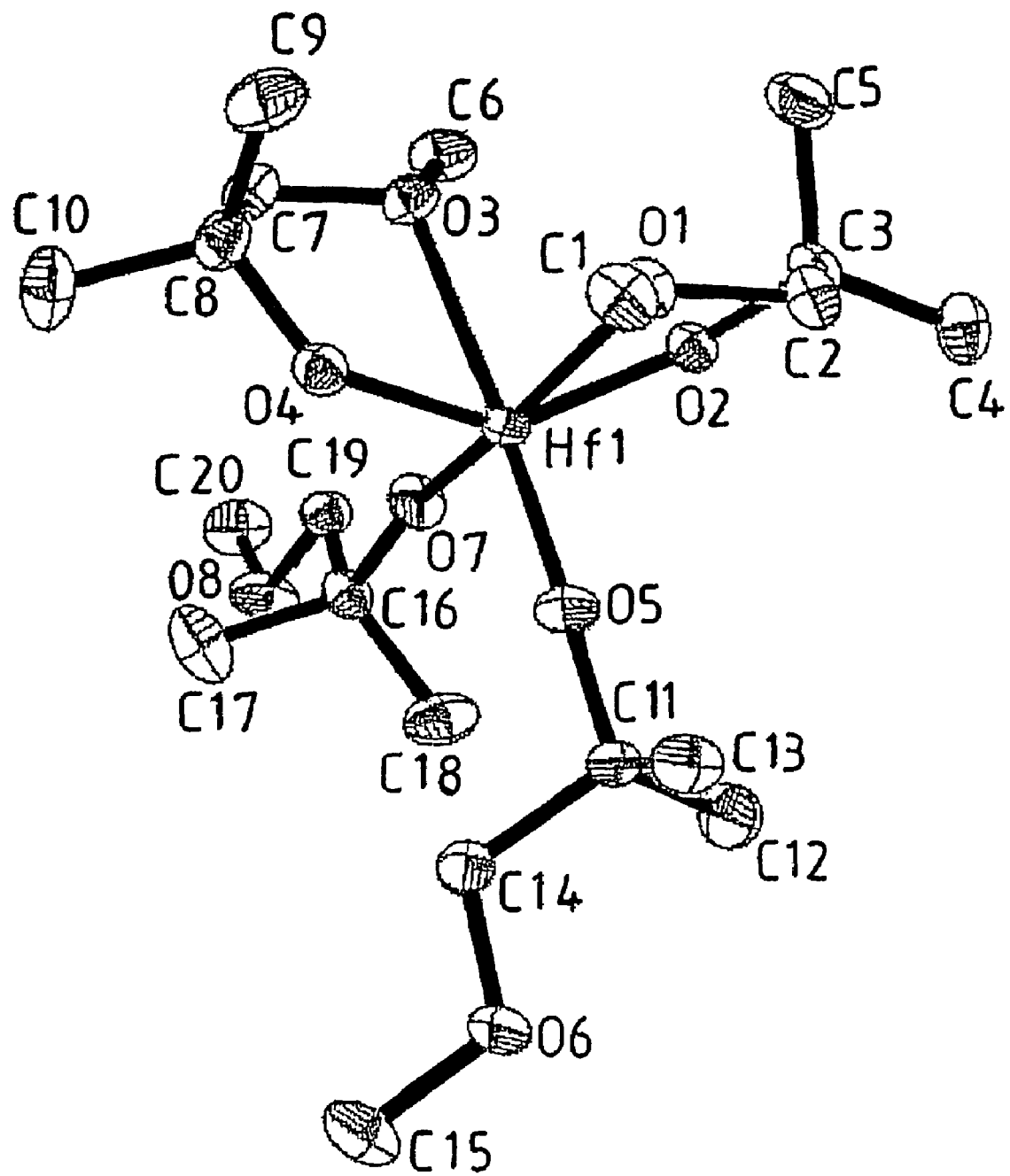
FIG. 2 shows the molecular structure of Hf(mmp)$_4$. Zr(mmp)$_4$ has a similar structure.

An envisaged structure for Hf(mmp)$_4$ is shown in FIG. 2 of the accompanying drawings.

EXAMPLE 5

Preparation of Zr(OPr$^i$)$_2$(mmp)$_2$ 1.06 g (2.75 mmol) Zr(OPr$^i$)$_4$·Pr$^i$OH was dissolved in hexane (ca 40 ml). 1-methoxy-2-methyl-2-propanol [mmpH] (0.65 ml, 0.57 g, 5.5 mmol) was added dropwise, the mixture was heated to reflux and stirring continued for a further 2 hours. The solution was cooled to room temperature and the volatiles removed by evaporation under reduced pressure. The product was isolated as a white viscous oil.

Microanalysis: Calc. C: 46.23; H: 8.73. Found: C: 44.17; H, 8.47;

$^1$H NMR (400 MHz, d$_8$-tol): 1.26 (s, OC(CH$_3$)$_2$CH$_2$OCH$_3$), 1.32 (d, OCH(CH$_3$)$_2$), 3.26 (2, OC(CH$_3$)$_2$CH$_2$OCH$_3$), 3.36 (s, OC(CH$_3$)$_2$CH$_2$OCH$_3$), 4.46 (m, OCH(CH$_3$)$_2$).

$^{13}$C NMR (100 MHz, d$_8$-tol): 32.1 (OC(CH$_3$)$_2$CH$_2$OCH$_3$), 34.2 (OCH(CH$_3$)$_2$), 64.9 (OC(CH$_3$)$_2$CH$_2$OCH$_3$), 76.1, 76.4 (OCH(CH$_3$)$_2$ and OC(CH$_3$)$_2$CH$_2$OCH$_3$), 88.6 (OC(CH$_3$)$_2$CH$_2$OCH$_3$).

IR: (ν cm$^{-1}$, Nujol, NaCl) 3589(w), 3423(w), 2724(w), 2282(w), 1239(w), 1175(m), 1115(m), 1019(m), 959(m).

EXAMPLE 6

Preparation of Ti(OPr$^i$)$_2$(mmp)$_2$

MmpH (2.81 g, 27 mmol) was added dropwise to 0.0135 moles) to a stirred solution of Ti(OPr$^i$)$_4$ (3.84 g, 13.5 mmol) in hexane (20 ml). The mixture was boiled under reflux for 1½ hours and was then allowed to cool. The solvent was then removed in vacuo to give Ti(OPr$^i$)$_2$(mmp)$_2$ as a colourless oil.

Microanalysis for TiC$_{16}$H$_{36}$O$_4$: (calculated) C,% 51.61; H,% 9.75; (experimental) C,% 51.20; H,% 9.92.

$^1$H NMR (C$_6$D$_5$CD$_3$ at 30° C.) δ 1.1 (26H, d, (CH$_3$)$_2$CH; CH$_3$OCH$_2$(CH$_3$)$_2$C); δ 3.2 (10H, two singlets, CH$_3$OCH$_2$(CH$_3$)$_2$C ); δ 4.5,(2H, m, (CH$_3$)$_2$CH).

$^{13}$C{$^1$H} NMR (C$_6$D$_5$CD$_3$, 30° C.): 32 (OC(CH$_3$)$_2$CH$_2$OCH$_3$), 33.4 (OCH(CH$_3$)$_2$), 64.4 (OC(CH$_3$)$_2$CH$_2$OCH$_3$), 81.7 (OC(CH$_3$)$_2$CH$_2$OCH$_3$ 86.5 (OCH(CH$_3$)$_2$), 88 (OC(CH$_3$)$_2$CH$_2$OCH$_3$).

IR (Nujol, cm$^{-1}$) 2972s, 2928s, 2869s, 2625w, 1463m, 1376m, 1360m, 1331m, 1277m, 1126s, 1001s, 850s, 778m., 629s.

EXAMPLE 7

Preparation of Ti(mmp)$_4$

MmpH (4.41 g, 42 mmol) was added dropwise to a stirred solution of Ti(NEt$_2$)$_4$ (2.85 g; 3 ml; 8.47 mmole) in hexane (20 ml) resulting in pale brown solution. The mixture was boiled under reflux for 1½ hours, allowed to cool, and then volatiles were removed in vacuo to give Ti (mmp)$_4$ as a pale brown oil.

Microanalysis for TiC$_{20}$H$_{44}$O$_8$: (calculated) C,% 52.17; H,% 9.63; (experimental) C,% 51.95; H,% 9.97.

$^1$H NMR (C$_6$D$_5$CD$_3$ at 30° C.) δ 1.3 (24H, s, CH$_3$OCH$_2$(CH$_3$)$_2$C); δ 3.2 (20H, two singlets, CH$_3$OCH$_2$(CH$_3$)$_2$C). VT $^1$H NMR showed sharp distinct peaks from −50 to +50° C.—no broadening was apparent.

$^{13}$C{$^1$H} NMR (C$_6$D$_5$CD$_3$, 30° C.): 31.9 (OC(CH$_3$)$_2$CH$_2$OCH$_3$), 64.5 (OC(CH$_3$)$_2$CH$_2$OCH$_3$), 81.7 (OC(CH$_3$)$_2$CH$_2$OCH$_3$), 87 (OC(CH$_3$)$_2$CH$_2$OCH$_3$).

IR (Nujol, cm$^{-1}$) 2975s, 2931s, 2876s, 2829m, 2625w, 1461m, 1360s, 1331m, 1277m, 12406m, 1116s, 1004s, 850m., 796s, 775s, 625s.

EXAMPLE 8

Preparation of La(mmp)$_3$

[La{N(SiMe$_3$)$_2$}$_3$] (2.89 g, 4.6 mmol) was dissolved in toluene (50 ml) and mmpH (2.2 ml, 1.96 g, 18.7 mmol) added dropwise under stirring. Stirring was continued at room temperature for a further 21 hours and the volatiles removed in vacuo to give the product as a brown viscous oil (Yield=1.8 g 87% with respect to La)

Microanalysis for LaC$_{15}$H$_{33}$O$_6$(calculated) C, % 40.18; H, % 7.43; (experimental) C, % 40.01; H % 7.38

EXAMPLE 9

Zirconium Oxide and Hafnium Oxide Deposition From Zr(OBu$^t$)$_2$(mmp)$_2$, Zr(mmp)$_4$, Hf(OBu$^t$)$_2$(mmp)$_2$ and Hf(mmp)$_4$ All four complexes were found to be excellent precursors for the deposition of ZrO$_2$ and HfO$_2$ thin films by MOCVD. The ZrO$_2$ and HfO$_2$ films were deposited by liquid injection MOCVD using the same general conditions shown in Table 1 below.

TABLE 1

Growth conditions used for the growth of ZrO$_2$ or HfO$_2$ thin films by liquid injection MOCVD using Zr(OBu$^t$)$_2$(mmp)$_2$, Zr(mmp)$_4$, Hf(OBu$^t$)$_2$(mmp)$_4$ or Hf(mmp)$_4$

| | |
|---|---|
| Substrate temperature | 350-650° C. |
| Reactor pressure | 20-30 mbar |
| Precursor solution concentration | 0.1M in toluene |
| Precursor solution injection rate | 4-8 cm$^3$ hr$^{-1}$ |
| Evaporator temperature | 130-150° C. |
| Argon carrier gas flow rate | 400-600 cm$^3$ min$^{-1}$ |
| Oxygen flow rate | 100-150 cm$^3$ min$^{-1}$ |
| Substrates | Si(100) |
| Oxide growth rate | 0.35-0.50 μm hr$^{-1}$ |

Figure 3:
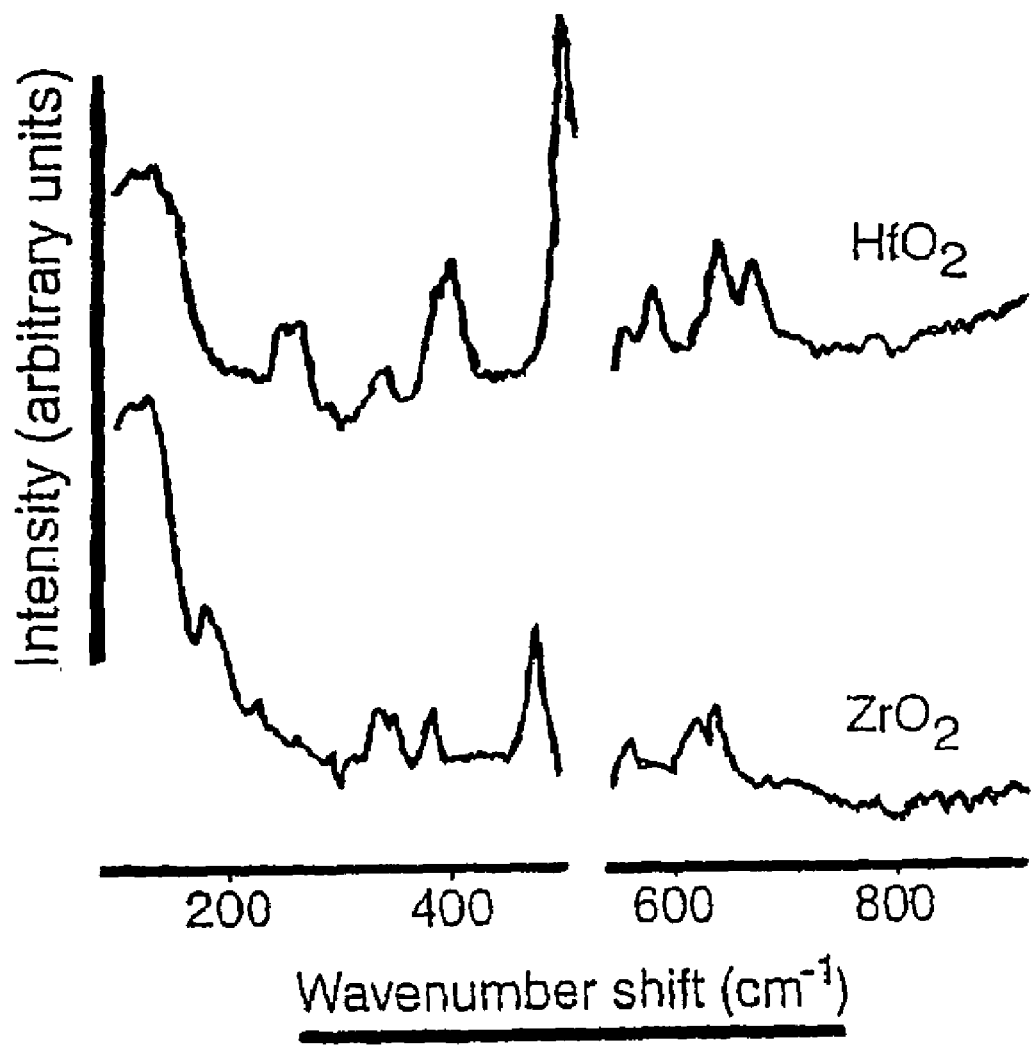
FIG. 3 shows laser Raman spectra ZrO$_2$ and HfO$_2$ films grown by liquid injection MOCVD using Zr(OBu$^t$)$_2$(mmp)$_2$ or Hf(OBu$^t$)$_2$(mmp)$_2$.

The identity of the films was confirmed as ZrO$_2$ or HfO$_2$ by laser Raman spectroscopy (see FIG. 3). Raman spectra of ZrO$_2$ and HfO$_2$ films grown from Zr(OBu$^t$)$_2$(mmp)$_2$ or Hf(OBu$^t$)$_2$(mmp)$_2$ are shown in FIG. 3. Comparison with bulk crystalline data showed that these films were predominantly in the α- or monoclinic phase.

The invention claimed is:

1. A precursor for use in a MOCVD process having the following general formula:

$$M(L)_x[OCR^1(R^2)CH_2X]_{4-x}$$

wherein M is a metal selected from Ti, Zr and Hf, L is a ligand, x is a number from 0 through 3 inclusive, $R^1$ is H or an alkyl group, $R^2$ is an optionally substituted alkyl group, and X is OR, wherein R is an alkyl group or a substituted alkyl group.

2. The precursor according to claim 1, wherein the ligand L is an alkoxy group having from 1 to 4 carbon atoms.

3. precursor according to claim 2, wherein the ligand L is selected from tertiary-butoxide and iso-propoxide.

4. The precursor according to claim 1, wherein $[OCR^1(R^2)CH_2X]$ is 1-methoxy-2-methyl-2-propanolate.

5. The precursor according to claim 1, wherein $[OCR^1(R^2)CH_2X]$ is selected from the group consisting of OCH(Me)CH$_2$OMe, OCEt$_2$CH$_2$OMe, OCH(Bu$^t$)CH$_2$OEt, OC(Bu$^t$)$_2$CH$_2$OEt, OC(Pr$^i$)$_2$CH$_2$OEt, OC(Pr$^i$)$_2$CH$_2$OC$_2$H$_4$OMe and OC(Bu$^t$)(CH$_2$Opr$^i$)$_2$.

6. The precursor according to claim 1, wherein said precursor is Zr(OBu$^t$)$_2$(mmp)$_2$.

7. The precursor according to claim 1, wherein said precursor is Zr(mmp)$_4$.

8. The precursor according to claim 1, wherein said precursor is Hf(OBu$^t$)$_2$(mmp)$_2$.

9. The precursor according to claim 1, wherein said precursor is Hf(mmp)$_4$.

10. A method of making a Ti-. Zr- or Hf-based precursor for use in a MOCVD process comprising reacting HOCR$^1$(R$^2$)CH$_2$X with the corresponding metal alkoxide or metal alkylamide in appropriate molar proportions; wherein R$^1$ is H or an alkyl group, R$^2$ is an optionally substituted alkyl group and X is selected from OR and NR$_2$ wherein R is an alkyl group or a substituted alkyl group.

11. A precursor for use in a MOCVD process having the following general formula:

$$La[OCR^1(R^2)CH_2X]_3$$

wherein R$^1$ is H or an alkyl group, R$^2$ is an optionally substituted alkyl group and X is selected from OR and NR$_2$, wherein R is an alkyl group or a substituted alkyl group.

12. The precursor according to claim 11, wherein [OCR$^1$(R$^2$)CH$_2$X] is 1-methoxy-2-methyl-2-propanolate.

13. The precursor according to claim 12, wherein [OCR$^1$(R$^2$)CH$_2$X] is selected from the group consisting of OCH(Me)CH$_2$OMe, OCEt$_2$CH$_2$OMe, OCH(Bu$^t$)CH$_2$OEt, OC(Bu$^t$)$_2$CH$_2$OEt, OC(Pr$^i$)$_2$CH$_2$OEt, OCH(Bu$^t$)CH$_2$NEt$_2$, OC(Pr$^i$)$_2$CH$_2$OC$_2$H$_4$OMe and OC(Bu$^t$)(CH$_2$OPr$^i$)$_2$.

14. A method of making a precursor as claimed in claim 11 comprising reacting HOCR$^1$(R$^2$)CH$_2$X with La{N(SiMe$_3$)$_2$}$_3$ in appropriate molar proportions.

15. A method of depositing single or mixed oxide layers or films by MOCVD, in which a precursor is contained in a metalorganic bubbler; or by liquid injection MOCVD, in which a precursor is dissolved in an appropriate inert organic solvent and then evaporated into the vapor phase using a heated evaporator, wherein at least one of the precursors is as defined in claim 1.

16. A method of providing a ZrO$_2$, ZrSO, HfO$_2$, HfSO, TiO$_2$, or TiSO film on a silicon substrate, the method comprising using metalorganic chemical vapor deposition to deposit the metal oxide, wherein the deposition utilizes a precursor material of the formula:

$$M(L)_x[OCR^1(R^2)CH_2X]_{4-x}$$

wherein M is a metal selected from Ti, Zr and Hf, L is a ligand, x is a number from 0 through 3 inclusive, R$^1$ is H or an alkyl group, R$^2$ is an optionally substituted alkyl group, and X is selected from OR and NR$_2$, wherein R is an alkyl group or a substituted alkyl group.

17. A method according to claim 16, wherein the ligand L is an alkoxy group having from 1 to 4 carbon atoms.

18. A method of providing a LaO$_2$ or LaSO film on a silicon substrate, the method comprising using metalorganic chemical vapor deposition to deposit the metal oxide, wherein the deposition utilizes a precursor material of the formula:

$$La[OCR^1(R^2)CH_2X]_3$$

wherein R$^1$ is H or an alkyl group, R$^2$ is an optionally substituted alkyl group and X is selected from OR and NR$_2$, wherein R is an alkyl group or a substituted alkyl group.

19. The method according to claim 18, wherein said precursor is La(mmp)$_3$.

* * * * *

UNITED STATES PATENT AND TRADEMARK OFFICE
CERTIFICATE OF CORRECTION

| | | |
|---|---|---|
| PATENT NO. | : 7,419,698 B2 | Page 1 of 1 |
| APPLICATION NO. | : 10/493667 | |
| DATED | : September 2, 2008 | |
| INVENTOR(S) | : Anthony Copeland Jones | |

It is certified that error appears in the above-identified patent and that said Letters Patent is hereby corrected as shown below:

On the cover page,

Item [*] Notice:  Subject to any disclaimer, the term of this patent is extended or adjusted under 35 USC 154(b) by (259) days Delete the phrase "by 259 days" and insert -- by 386 days --

Signed and Sealed this

Twenty-eighth Day of July, 2009

JOHN DOLL
*Acting Director of the United States Patent and Trademark Office*